United States Patent [19]
Rachlin et al.

[11] Patent Number: 5,234,932
[45] Date of Patent: Aug. 10, 1993

[54] SUBSTITUTED QUINOLINES AND LEUCOTRIENE ANTAGONISM TREATMENT THEREWITH

[75] Inventors: Schneur Rachlin, Værløse; Erik T. Hansen, Fredensborg, both of Denmark

[73] Assignee: Leo Pharmaceutical Products ltd., Ballerup, Denmark

[21] Appl. No.: 828,795

[22] PCT Filed: Aug. 9, 1990

[86] PCT No.: PCT/DK90/00201
§ 371 Date: Jan. 29, 1992
§ 102(e) Date: Jan. 29, 1992

[87] PCT Pub. No.: WO91/03466
PCT Pub. Date: Mar. 21, 1991

[30] Foreign Application Priority Data
Aug. 29, 1989 [GB] United Kingdom ............ 8919504

[51] Int. Cl.$^5$ .................. C07D 403/10; C07D 215/12
[52] U.S. Cl. .................. 514/311; 514/314; 546/176; 546/172; 546/174; 546/175; 546/180
[58] Field of Search ............... 546/176, 172, 174, 175, 546/180; 514/311, 314

[56] References Cited

U.S. PATENT DOCUMENTS

| | | | |
|---|---|---|---|
| 4,920,131 | 4/1990 | Huang et al. | 514/311 |
| 4,920,132 | 4/1990 | Huang et al. | 514/314 |

FOREIGN PATENT DOCUMENTS

| | | |
|---|---|---|
| 8904305 | 5/1989 | European Pat. Off. |
| 8905294 | 6/1989 | European Pat. Off. |

Primary Examiner—David B. Springer
Attorney, Agent, or Firm—Cushman, Darby & Cushman

[57] ABSTRACT

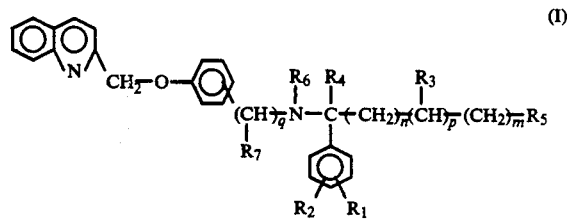

The present invention relates to hitherto unknown compounds of formula, in which m and n stand for an integer from 0–5, p stands for 0 or 1, and q stands for an integer from 0–4, $R_1$ and $R_2$ are the same or different and stand for hydrogen, halogen, nitro, amino, alkyl or alkoxy; $R_3$ is hydroxy, hydrogen, straight or branched, saturated or unsaturated $C_1$–$C_6$ alkyl; $R_5$ stands for an acidic group, e.g. carboxy, 1-H tetrazolyl, a sulphonic acid group, a sulfamyl group, a sulphinic acid group, or a hydroxamic acid group; $R_4$ and $R_6$ are the same or different and stand for hydrogen, straight or branched, saturated or unsaturated, unsubstituted or substituted $C_1$–$C_6$ alkyl groups or unsubstituted or substituted aralkyl groups. $R_7$ has the same meaning as $R_5$ or represents a hydrogen, straight or branched, saturated or unsaturated, unsubstituted or substituted $C_1$–$C_6$-alkyl group. The present compounds are of value in the human and veterinary practice as lipoxygenase inhibitors and/or leukotriene antagonists.

5 Claims, No Drawings

SUBSTITUTED QUINOLINES AND LEUCOTRIENE ANTAGONISM TREATMENT THEREWITH

The present invention relates to hitherto unknown compounds useful in the human and veterinary therapy, to pharmaceutically acceptable salts thereof, to bioreversible derivatives thereof, to methods for producing said new compounds, to pharmaceutical compositions containing the new compounds, to dosage units of the compositions, and to methods of treating patients using said compositions and dosage units.

It has recently been discovered that leukotrienes, which are formed via the 5-lipoxygenase pathway of arachidonic acid metabolism, are implicated in a variety of pathophysiologic functions, such as bronchoconstriction, plasma exudation, coronary artery spasm, leukocyte chemotaxis and neutrophil degranulation (1). It is therefore of considerable interest to develop compounds which inhibit 5-lipoxygenases and thereby the production of leukotrienes, or antagonize the effects of leukotrienes.

(1) P.J. Piper and M.N. Samhoun, Br.Med.Bull. 43 (1987) 297.

German patent application DE 3607 382 (corresponding to United Kingdom patent application No. 8604183) describes a series of pyridylmethoxy or -methylthio substituted N-substituted aniline derivatives with activities as lipoxygenase inhibitors and/or leukotriene antagonists. The N-substituent in these compounds may be substituted or unsubstituted aryl or aralkyl, and international patent application No. PCT/DK88/10188 further illustrates that introduction of one of a number of acidic groups into the phenyl ring of these aryl or aralkyl N-substituents results in compounds with a more pronounced effect.

Now it has surprisingly turned out that compounds without such an acidic substituent in the phenyl ring but containing an acidic group placed in the alkyl chain of an aralkyl N-substituent have an even more pronounced effect.

Moreover, these compounds are more specific agents, as their leukotriene antagonistic activity is much more pronounced than their activity as lipoxygenase inhibitors.

Also, a number of the present compounds are well absorbed after enteral administration.

The present compounds have the formula I

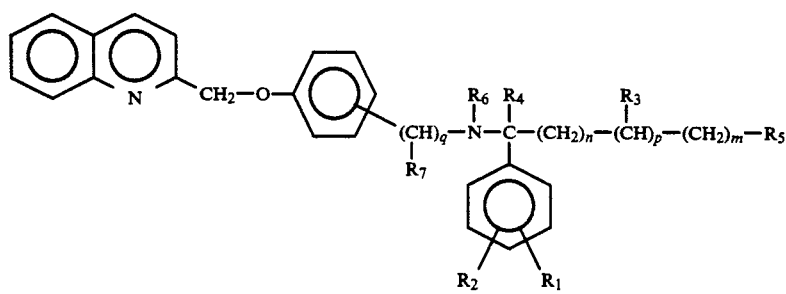

I in which m and n stands for an integer from 0–5, p stands for 0 or 1, and q stands for an integer from 0–4, $R_1$ and $R_2$ are the same or different and stand for hydrogen, halogen, nitro, amino, alkyl or alkoxy; $R_3$ is hydroxy, hydrogen, straight or branched, saturated or unsaturated $C_1$–$C_6$ alkyl; $R_5$ stands for an acidic group, e.g. carboxy, 1-H tetrazolyl, a sulphonic acid group, a sulfamyl group, a sulphinic acid group, or a hydroxamic acid group; $R_4$ and $R_6$ are the same or different and stand for hydrogen, straight or branched, saturated or unsaturated, unsubstituted or substituted $C_1$–$C_6$ alkyl groups or unsubstituted or substituted aralkyl groups.

$R_7$ has the same meaning as $R_5$ or represents a hydrogen, straight or branched, saturated or unsaturated, unsubstituted or substituted $C_1$–$C_6$-alkyl group.

Among the preferred compounds of the invention are those of formula I, in which $R_5$ stands for a carboxy group.

Some of the compounds described herein contain one or more centers of asymmetry and may thus give rise to diastereoisomers and optical isomers. The present invention is meant to comprehend such possible diastereoisomers as well as their racemic and resolved optically active forms.

The present salts of the compounds of formula I may be formed with pharmaceutically acceptable inorganic or organic acids, such as hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, without these examples being considered limiting for the invention.

The present salts of the compounds of formula I may also be formed with pharmaceutically acceptable, inorganic or organic bases. As examples of salts formed with pharmaceutically acceptable, non-toxic bases, mention may be made of alkali metal salts and alkaline earth metal salts, such as lithium, sodium, potassium, magnesium, calcium salts, as well as salts with ammonia and suitable non-toxic amines, such as $C_1$–$C_6$-alkylamines, e.g. triethylamine, $C_1$–$C_6$-alkanolamines, e.g. diethanolamine or triethanolamine, procaine, cycloalkylamines, e.g. dicyclohexylamine, benzylamines, e.g. N-methylbenzylamine, N-ethylbenzylamine, N-benzyl-β-phenethylamine, N,N'-dibenzylethyldenediamine or dibenzylamine, and heterocyclic amines, e.g. morpholine, N-ethylpiperidine and the like.

Even if the present compounds are well absorbed after enteral administration, in some cases it can be advantageous to prepare suitable bioreversible derivatives of compounds of the invention, i.e. to prepare so-called prodrugs, preferably derivatives, the physiochemical properties of which leads to improved solubility at physiological pH and/or absorption of the compound in question.

Such derivatives are for instance esters of N-hydroxymethyl derivatives of compounds of the invention, such compounds being prepared by reaction of a secondary aminefunction of compounds of the invention with formaldehyde (2,3,4,5) followed by reaction with a suitable acidic compound or activated derivatives of such compounds, for instance with bisulfite (6), N,N-dimethylglycine, N,N-diethyl-β-alanine, or phosphoric acid (7), but other suitable acids which form bioreversible derivatives with desirable physiocochemical properties can be used as well.

(2) R.G. Kallen and W.P. Jencks, J. Biol. Chem. 241 (1966) 5864.
(3) C.J. Martin and M.A. Marini, J. Biol. Chem. 242 (1967) 5736.
(4) M. Levy and D.E. Silberman, J. Biol. Chem. 118 (1937) 723.
(5) S. Lewin and D.A. Humphany, J. Chem. Soc. B (1966) 210.
(6) B.C. Jain, B.H. Iyer, and P.C. Guha, Science and Culture 11 (1946) 568.
(7) S.A. Varia, S. Schuller, K.B. Sloan and V.J. Stella, J. Pharm. Sci., 73 (1985) 1068 and following papers.

Further examples include esters formed with the acidic function in the molecule, such as simple esters, e.g. methyl or ethyl, acyloxyalkyl, alkoxycarbonyloxyalkyl or aminoacyloxyalkyl esters, which are readily hydrolyzed in vivo or in vitro.

Among the above esters the following are preferred: alkanoyloxymethyl with from 3 to 8 carbon atoms, 1-(alkanoyloxy)ethyl with from 4 to 9 carbon atoms, alkoxycarbonyloxymethyl with from 3 to 6 carbon atoms, 1-(alkoxycarbonyloxy)ethyl with from 4 to 7 carbon atoms, and α-aminoalkanoyloxymethyl with from 2 to 6 carbon atoms.

Other preferred esters are lactonyl esters, e.g. 3-phthalidyl, 4-crotonolactonyl or γ-butyrolacton-4-yl esters.

Also within the scope of the invention are methoxymethyl, cyanomethyl, or mono- or dialkyl substituted aminoalkyl esters, e.g. 3-dimethylaminoethyl, 2-diethylaminoethyl, or 3-dimethylaminopropyl esters.

In particular, such esters are preferred which are well absorbed upon enteral administration and during or after the absorption are hydrolysed to the compounds of formula I.

These examples are not to be considered as limiting for the invention, and other suitable methods to improve the physicochemical properties and solubility of the compounds concerned can be used as well.

Metabolites of arachidonic acid include prostaglandins and leukotrienes. Both of these two groups of metabolites are important in the pathophysiology of inflammatory and allergic reactions. Many inhibitors of prostaglandin synthesis are known and are being used as antiinflammatory agents (8), but relatively few leukotriene inhibitors are presently known, and they are generally not clinically acceptable. The first step in the biochemical synthesis of all leukotrienes is the peroxidation at the 5-carbon atom of arachidonic acid. This reaction is catalyzed by the enzyme 5-lipoxygenase, present mainly in leukocytes. Leukotriene $B_4$ is one of the most potent chemoattractants for polymorphonuclear leukocytes, and at the same time causes aggregation and degranulation of these inflammatory cells. It is thus a potent pro-inflammatory hormone. Leukotriene $C_4$, $D_4$, and $E_4$ together comprise the agent known previously as "slow-reacting substance of anaphylaxis" (SRS-A), which is three orders of magnitude more potent than histamine in causing bronchoconstriction, and also regulates microvascular smooth muscle contractility and permeability. It is therefore a mediator of asthmatic, allergic and inflammatory reactions.

(8) R.J. Flower, S. Moncada and J.R. Vane, in: The Pharmacological Basis of Therapeutics (1980), eds. A.G. Gilman, L.S. Goodmann and A. Gilman, (Macmillan, N.Y.) p. 682.

Inhibition of 5-lipoxygenase thus leads to a decrease in the formation of all of these inflammatory and allergic mediators. This has very important clinical implications, as specific 5-lipoxygenase inhibitors and leukotriene antagonists are of potential interest in the therapy of asthma, allergy, rheumatoid arthritis, spondyloarthritis, gout, atherosclerosis, proliferative and inflammatory skin disorders, such as psoriasis and atopic dermatitis, chronic inflammatory bowel disease, and other inflammatory conditions, vasospasm associated with angina pectoris, pulmonary hypertension, cystic fibrosis, the adult respiratory distress syndrome, ischemic and reperfusion injury etc. (9). The identification of specific 5-lipoxygenase inhibitors and leukotriene antagonists is thus a novel approach with very wide implications for the treatment of a diversity of clinical disorders.

(9) E.J. Goetzyl, D.G. Payan and D.W. Goldman, J. Clin. Immunol. 4 (1984) 79.

The following method was used to assay 5-lipoxygenase activity in vitro: Rat peritoneal cells were harvested by i.p. injection of 10 ml Hank's balanced salt solution (GIBCO, cat No. 4025, U.S.A.) containing 12.5 U/ml sodium heparin (Leo, Denmark) in anaesthesized rats. The resulting cell suspension, which mainly contained macrophages, was transferred to a test tube and washed twice by centrifugation (200 g, 10 min.) and resuspended in Hank's balanced salt solution containing 0.5% bovine serum albumin (BSA) (Sigma Chem. Co., U.S.A.). The cells from 9 rats were finally resuspended in Hank's balanced salt solution (with BSA) containing 5μCi [1-$^{14}$C]arachidonic acid (The Radiochemical Centre, Amersham, U.K.) and incubated for 90 minutes at 37° C. This caused labelling of cell membrane phospholipids as radioactive arachidonic acid was incorporated in the 2-position of the glycerol moiety. Excess arachidonic acid was then removed by washing the cells twice as described above. The cells were finally resuspended in the same solution (without BSA) at $10^7$ cells/ml. 475 μl of the cell suspension was preincubated at 37° C. for 5 minutes with either 5 μl dimethylsalphoxide (DMSO) (control tube), or 5 μl of a drug solution in DMSO. Then 20 μl of a mixture of equal volumes of the calcium ionophore A23187, $10^{-4}$M in ethanol (Calbiochem, U.S.A.), and 0.4M $CaCl_2$ in water was added. The final concentration of A23187 was thus $2\times10^{-6}$M, and of $Ca^{++}$ 8 mM. After 5 minutes of incubation the tubes were transferred to an ice-bath and centrifuged for 10 minutes at 3,000 g (4° C.). An aliquot of the supernatant was counted by liquid scintillation spectrometry in order to calculate the total radioactive release induced by A23187 in presence of drugs. A decrease in radioactive release was taken as indication of phospholipase $A_2$ inhibition. The supernatant was then extracted with ethyl acetate (2 ml), adjusted to pH 3 with 1N HCl and further extracted with 2 ml ethyl acetate. The combined extracts were evaporated to dryness in vacuo, the residue was redissolved in a small volume of methanol and applied by means of a Desaga Autospotter™ to a silica-gel coated thin-layer plate fitted with a polar concentrating zone (Merck Art. 11798, Darmstadt, F.R.G.). The plates were developed in the organic layer of the solvent mixture ethyl acetate/acetic acid/isooctane/water (55:10:25:50). Radioactive spots were detected by autoradiography (AGFA-GEVAERT, Osray-RPI X-ray film, Belgium), and changes induced by drugs in the metabolic pattern of arachidonic acid were quantified by a laser densitometer (LKB, Ultroscan ™ 2202, Bromma, Sweden) in combination with an integrating computer (SP 4100, Spectra-Physics, San Jose, Calif., U.S.A.).

These cells produced measurable amounts of radioactive 6-keto-prostaglandin $F_{1\alpha}$, thromboxane $B_2$, prostaglandin $D_2$, hydroxyheptadecatrienoic acid (HHT) (all cyclooxygenase products), 5-hydroxyeicosatetraenoic acid (5-HETE) and leukotriene $B_4$ (both 5-lipoxygenase products).

When a compound produced according to one of the Examples 9 or 11 at a final concentration of $10^{-6}$M was added to the reaction mixture described above, a significant and specific decrease in the production of leukotriene $B_4$ and 5-HETE occurred. At the same time, a decrease in synthesis of the cyclooxygenase products HHT, prostaglandin $D_2$, thromboxane $B_2$ and 6-keto-prostaglandin $F_{1\alpha}$ was not observed. This pattern of drug activity is indicative of truly specific 5-lipoxygenase inhibition.

Leukotriene antagonists may be identified by observing the contractions elicited in preparations of guinea-pig ileum strips suspended in a physiological buffer by addition of pure leukotriene $D_4$ ($LTD_4$) (10). The ileum strips are connected to an isotonic transducer, and the contractions are continuously recorded on a multichannel recorder. Before addition of $LTD_4$, atropine and indomethacin are added to the buffer in order to block any cholinergic or prostaglandin mediated contractile effects. Test compounds to be studied with respect to leukotriene antagonism are dissolved in DMSO and added to the organ bath 2 minutes prior to addition of $LTD_4$ at $10^{-9}$M (final concentration), the final concentration of DMSO being 0.1%, a concentration which can be shown not to affect the ileum response to $LTD_4$. The test compounds may be added at various concentrations, often beginning at $10^{-}$M and then decreasing the concentration in case of antagonism.

When the compounds of the present invention were added to the ileum preparation before addition of $LTD_4$ a significant inhibition occurred of the specific $LTD_4$-induced contraction. In several cases this inhibition occurred at concentrations in the submicromolar range, e.g. with a compound according to one of the Examples 1-4, 12-15, 17, 25-43. On other hand, contractions induced with histamine at $10^{-7}$M were not inhibited by these compounds even at micromolar concentrations.

Leukotriene antagonists may be further characterized using guinea-pig tracheal strips instead of ileum strips (10). In this relevant in vitro model of human airways (11) tracheal strips are suspended in a physiological buffer containing indomethacin. A concentration-response curve to $LTD_4$ is generated in the presence and absence of the leukotriene antagonists. From these curves the potency of a leukotriene antagonist may be expressed as the $pK_B$ value, the negative logarithm of the antagonist dissociation constant. The $pK_B$ value is determined as $-\log([\text{antagonist}]/(\text{dose ratio} -1))$, where the dose ratio is defined as $EC_{50}$ (presence of antagonist)/$EC_{50}$ (absence of antagonist) and $EC_{50}$ refers to the concentration of $LTD_4$ eliciting 50% of the maximum response to $LTD_4$ (12). This is the generally accepted way of expressing leukotriene antagonistic potency independent of $LTD_4$ concentration. $pK_B$ values for the compounds according to the Examples 1 and 15 were found to be 9.7 and 9.0.

(10) I. Ahnfelt-Rønne, D. Kirstein and C. Kærgaard-Nielsen, European, J. Pharmacol. 155 (1988) 117.
(11) R.M. Muccitelli, S.S. Tucker, D.W.P. Hay, T.J. Torphy and M.A. Wasserman, J. Pharmacol. Exp. Ther. 243 (1987) 466.
(12) R.F. Furchogott, in: Handbook of Experimental Pharmacology, vol 33 (1982), eds. O. Eichler, A. Farah, H. Herken and A.D. Welch (Springer Verlag, N.Y.) p. 283.

It is of importance to investigate the receptor binding properties of leukotriene antagonists in relation to their $pK_B$ values (13), i.e. to correlate antagonist receptor blocking with inhibition of smooth muscle contraction.

Receptor binding studies may be performed with guinea-pig lung membranes in a direct competition assay between a leukotriene antagonist and [$^3$H]$LTD_4$ for binding to the $LTD_4$ receptor (10,13). A $pIC_{50}$ value is determined as the negative logarithm of the molar concentration of antagonist inhibiting [$^3$H]$LTD_4$ binding by 50%. $pIC_{50}$ values for the compounds according to the Examples 1 and 15 were found to be 8.6 and 7.8. These $pIC_{50}$ values were observed to correlate with the antagonist $pK_B$ values, proving that the inhibition of smooth muscle contraction by the present compounds in fact depends mechanistically on binding to the $LTD_4$ receptor.

(13) S. Mong, H.-L. Wu, M.O. Scott, M.A. Lewis, M.A. Clark, B.M. Weichman, C.M. Kinzig, J.G. Gleason and S.T. Crooke, J. Pharmacol. Exp. Ther. 234 (1985) 316.

The present invention also relates to a method for producing the present compounds.

In one embodiment, an amine of the formula II

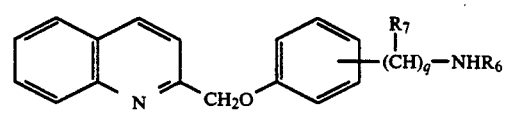

in which $R_6$, $R_7$, and q have the above meanings, is reacted with a compound of the formula III

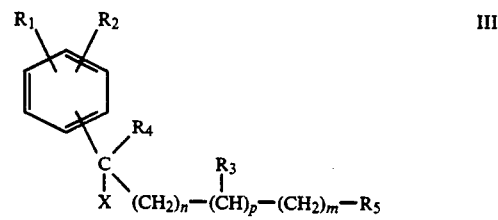

in which m, n, p, $R_1$, $R_2$, $R_3$, $R_4$, and $R_5$ have the above meanings, and X is capable of forming a "good leaving group", X thus standing for e.g. a halogen atoms, such as chlorine, bromine or iodine, or an alkyl- or arylsulphonyloxy group, but other leaving groups can be used as well, such as an alkylsulphate group, a chlorosulphonyloxy group, an alkylsulphite group, a mono- or dialkylphosphate group or a nitrate group, to form a compound of the formula I.

During the reaction $R_5$ may be protected with conventional protecting groups for instance in the case of a carboxyl group as an ester.

The reaction is performed in a suitable inert organic solvent, such as methanol or ethanol, but other solvents can be used as well. The reaction is preferably performed at ambient temperature, but in some cases it is convenient to cool the reaction mixture below room temperature, or to heat the reaction mixture above room temperature, up to the boiling point of the solvent used, depending on the nature of the reactants of the formulae II and III used. The crude reaction products of the formula I are collected by filtration, or are extracted from the reaction mixture with a suitable solvent, such as diethyl ether, ethyl acetate, dichloromethane or chloroform. The products are purified e.g. by recrystallization or by chromatography.

In another embodiment, an amine of the formula II is reacted with a compound of the formula IV

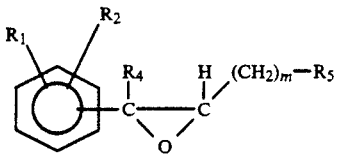

in which $R_1$, $R_2$, $R_4$, $R_5$, and m have the above meanings.

The reaction is performed either in a suitable inert organic solvent, such as methanol, ethanol, dimethylformamide or hexamethyl phosphoric triamide, and in water, or in mixtures thereof. The reaction is performed at a temperature about or above room temperature, up to the boiling point of the solvent used. In some cases it can, however, be convenient to cool the reaction mixture below room temperature, depending on the nature of the compound of the formula IV used. The isolation and purification of the products can be performed as described above.

In still another embodiment a compound of the formula V

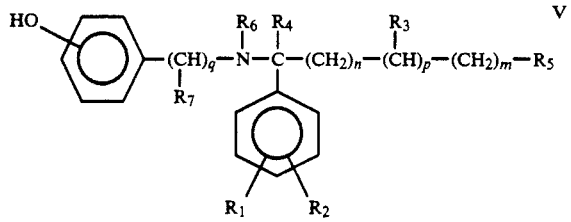

in which m, n, p, q, $R_1$, $R_2$, $R_3$, $R_4$, $R_5$, $R_6$, and $R_7$ have the above meanings, is reacted with a compound of the formula VI

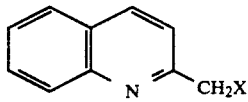

in which X have the above meanings, to form the desired compound of formula I.

The solvent and reaction conditions used are conveniently as described above for the alkylation of amines of the formula II, but other solvents and/or reaction conditions can be used as well, depending on the nature of the compounds of formulae V and VI which are reacted.

During the reaction $R_5$ may be protected with conventional protecting groups for instance in the case of a carboxyl group as an ester.

In a fourth embodiment, a compound of the formula VII

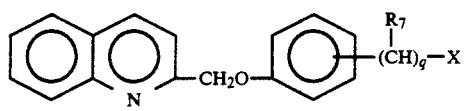

in which $R_7$ and X have the above meanings and q is 1-3, is reacted with a compound of the formula VIII

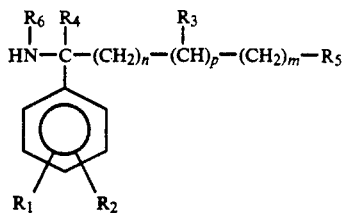

in which m, n, p, $R_1$, $R_2$, $R_3$, $R_4$, $R_5$, and $R_6$ have the above meanings, to give the desired compound of the invention. During the reaction $R_5$ and $R_7$, if acidic, may be protected with conventional protecting groups, for instance in case of being a carboxylic acid group being protected as an ester. The solvent and reaction conditions used are conveniently as described above the alkylation of amines of the formula II, but other solvents and/or reaction conditions can be used as well, depending on the nature of the compounds of formulae VII and VIII which are reacted. The isolation and purification of the products can be performed as described above.

In a fifth embodiment, a carbonyl compound of the formula IX

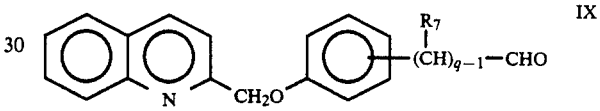

in which $R_7$ has the above meaning and q is 1-4, is reacted with an amine of the formula X

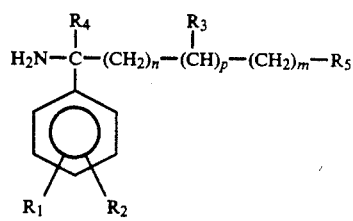

in which m, n, p, $R_1$, $R_2$, $R_3$, $R_4$, and $R_5$ have the above meanings, followed by hydrogenation in the presence of a suitable catalyst or by reduction e.g. with an alkali-metal borohydride. The hydrogenation or reduction can, if convenient be performed simultaneously with the reaction with the carbonyl compound, that is, without isolation of the intermediary so-called Schiff-base.

The reaction is performed in a suitable inert organic solvent, such as methanol or ethanol, but other solvents can be used as well. The reaction is preferably performed at ambient temperature, but in some cases it is convenient to col the reaction mixture below room temperature, or to heat the reaction mixture above room temperature, up to the boiling point of the solvent used, depending on the nature of the reactants of the formulae IX and X used. The isolation and purification of the products can be performed as described above.

Additionally, the acidic functionalities $R_5$ and $R_7$ can be prepared according to the following general reaction schemes:

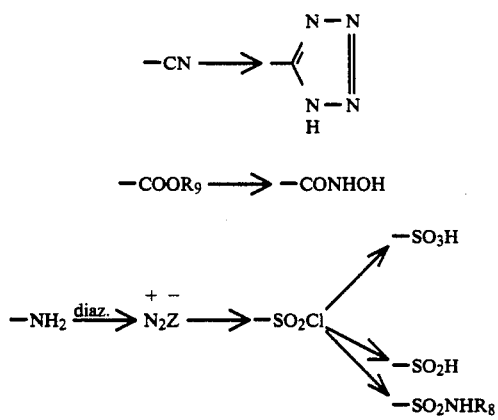

$R_8$ having the same meanings as $R_1$.

The present compounds are intended for use in pharmaceutical compositions which are useful in the treatment of the above mentioned diseases.

The amount required of a compound of formula (I) (hereinafter referred to as the active ingredient) for therapeutic effect will, of course, vary both with the particular compound, the route of administration and the mammal under treatment. A suitable dose of a compound of formula (I) for systemic treatment is 0.5 to 100 mg per kilogram bodyweight, the most preferred dosage being 0.5 to 50 mg/kg of mammal bodyweight, for example 5 to 25 mg/kg; administered once or more times daily.

In spray formulations, a suitable anti-asthmatic dose of a compound of formula (I) is 1 $\mu$g to 5 mg of compound per kilogram bodyweight, the most preferred dosage being 1 $\mu$g to 1 mg/kg of mammal bodyweight, for example from 1 $\mu$g to 0.5 mg/kg.

While it is possible for an active ingredient to be administered alone as the raw chemical, it is preferable to present it as a pharmaceutical formulation. Conveniently, the active ingredient comprises from 0.1% to 100% by weight of the formulation. Conveniently, dosage units of a formulation contain between 0.07 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such self-propelling powder-dispensing formulations described hereinafter), may comprise 0.1 to 20% w/w, for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and for human medical use, of the present invention comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

A tablet may be made by compressing or moulding the active ingredient optionally with one or more accessory ingredient. Compressed tablets may be prepared by compressing, in a suitable machine, the active ingredient in a free-flowing form, such as a powder or granules, optionally mixed with a binder, lubricant, inert diluent, surface active or dispersing agent. Moulded tablets may be made by moulding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Formulations suitable for topical administration include liquid or semi-liquid preparations, such as liniments, lotions, oil-in-water or water-in-oil emulsions, such as creams, ointments or pastes; or solutions or suspensions, such as drops. For example, for ophthalmic administration, the active ingredient may be presented in the form of aqueous eye drops as, for example, a 0.1-1.0% solution.

Formulations suitable for administration to the nose or buccal cavity include powder, self-propelling and spray formulations, such as aerosols and atomizers. The formulations, when dispersed, preferably have a particle size in the range of 10 to 100$\mu$.

Such formulations are most preferably in the form of a finely comminuted powder for pulmonary administration from a powder inhalation device or self-propelling powder-dispensing formulations, where the active ingredient, as a finely comminuted powder, may comprise up to 99.9% w/w of the formulation. In the case of self-propelling solution and spray formulations, the effect may be achieved either by choice of a valve having the desired spray characteristics (i.e. being capable of producing a spray having the desired particle size) or by incorporating the active ingredient as a suspended powder in controlled particle size. These self-propelling formulations may be either powder-dispensing formulations or formulations dispensing the active ingredient as droplets of a solution or suspension.

Self-propelling powder-dispensing formulations preferably comprise dispersed particles of solid active ingredients, and a liquid propellant having a boiling point below 18° C. at atmospheric pressure. The liquid propellant may be any propellant known to be suitable for medicinal administration and may comprise one or more $C_1$-$C_6$-alkyl hydrocarbons or halogenated $C_1$-$C_6$-alkyl hydrocarbons or mixtures thereof; chlorinated and flourinated $C_1$-$C_6$-alkyl hydrocarbons are especially preferred. Generally, the propellant constitutes 50 to 99.9% w/w of the formulation whilst the active ingredient constitutes 0.1 to 20% w/w, for example about 2% w/w, of the formulation.

The pharmaceutically acceptable carrier in such self-propelling formulations may include other constituents in addition to the propellant, in particular a surfactant or a solid diluent or both. Surfactants are desirable since they prevent agglomeration of the particles of active ingredient and maintain the active ingredient in suspension. Especially valuable are liquid non-ionic surfactants and solid anionic surfactants or mixtures thereof. Suitable liquid non-ionic surfactants are esters and partial esters of fatty acids with aliphatic polyhydric alcohols, for instance, sorbitan monooleate and sorbitan trioleate, known commercially as "Span 80" (Trade Name) and "Span 85" (Trade Name), respectively. The liquid non-ionic surfactant may constitute from 0.01 up to 20% w/w of the formulation, though preferably it constitutes below 1% w/w of the formulation. Suitable solid anionic surfactants include alkali metal, ammonium and amine salts of dialkyl sulphosuccinate (where the alkyl groups have 4 to 12 carbon atoms). the solid anionic surfactants may constitute from 0.01 up to 20% w/w of the formulation, though preferably below 1% w/w of the composition solid diluents may be advantageously incorporated in such self-propelling formulation where the density of the active ingredient differs substantially from the density of the propellant; also, they help to maintain the active ingredient in suspension. The solid diluent is in the form of a fine powder, preferably having a particle size of the same order as that of the particles of the active ingredient. Suitable solid diluents include sodium chloride, sodium sulphate and sugars.

Formulations of the present invention may also be in the form of a self-propelling formulation wherein the active ingredient is present as much in suspension or in solution. Such self-propelling formulations may comprise the active ingredient, propellant and co-solvent, and advantageously an anti-oxidant stabiliser. The propellant is one or more of these already cited above. Co-solvents are chosen for their solubility in propellant, their ability to dissolve the active ingredient, and for their having the lowest boiling point consistent with these above-mentioned properties. Suitable co-solvents are $C_1$-$C_6$-alkyl alcohols and ethers and mixtures thereof. The co-solvent may constitute 5 to 40% w/w of the formulation, though preferably less than 20% w/w of the formulation. Antioxidant stabilizers may be incorporated in such solutions-formulations to inhibit deterioration of the active ingredient and are conveniently alkali metal ascorbates or bisulphites. They are preferably present in an amount of up to 0.25% w/w of the formulation.

Such self-propelling formulations may be prepared by any method known in the art. For example, the active ingredient (either as particles as defined hereinabefore as such or in suspension in a suitable liquid or in up to 20% w/v solution in an acceptable cosolvent, as appropriate) is mixed with any other constituents of a pharmaceutically acceptable carrier. The resulting mixture is cooled, introduced in a suitable cooled container, and propellant is added thereto in liquid form; and the container is sealed. Alternatively, such self-propelling formulations may be prepared by mixing the active ingredient either in particles as hereinbefore defined or in 2 to 20% w/v alcohol or aqueous solution as appropriate, together with the remaining constituents of the pharmaceutically acceptable carrier other than the propellant; introducing the resulting mixture, optionally with some propellant, into a suitable container; and injecting the propellant, under pressure, into the container am ambient temperature through a valve which comprises a part of the container and is used to control release of the formulation from it. Desirably, the container is purged by removing air from it at a convenient stage in the preparation of the self-propelling formulation.

A suitable container for a self-propelling formulation is one provided with a manually-operable valve and constructed of aluminium, stainless steel or reinforced glass. The valve should, of course, be one having the desired spray characteristics of particle size as hereinbefore defined. Advantageously, the valve is of the type which delivers a fixed amount of the formulation on the occasion of each operation of the valve, for example, about 50 to 100 microliters of formulation in each delivery.

Formulations of the present invention may also be in the form of an aqueous or dilute alcoholic solution, optionally a sterile solution of the active ingredient for use in a nebuliser or atomizer, wherein an accelerated air stream is used to produce a fine mist consisting of small droplets of the solution. A buffering agent and a surface active agent may also be included in such a formulation which should also contain a preservative such as methylhydroxybenzoate.

Other formulations suitable for nasal administration include a fine powder having a particle size of 10 to 100 microns which is administered in the manner in which snuff is taken, i.e. by rapid inhalation through the nasal passage from a container of the powder held close up to the nose.

In addition to the aforementioned ingredients, the formulations of this invention may include one or more additional ingredients, such as diluents, buffers, flavouring agents, binders, surface active agents, thickeners, lubricants, preservatives, e.g. methylhydroxybenzoate (including anti-oxidants), emulsifying agents and the like.

The compositions may further contain other therapeutically active compounds usually applied in the treatment of the above mentioned pathological conditions, for instance glucocorticoids, anti-histamines, platelet activating factor (PAF) antagonists, anticholinergic agents, methyl xanthines, $\beta$-adrenergic agents, salicylates, indomethacin, flufenamate, naproxen, timegadine, gold salts, penicillamine, serum cholesterol-reducing agents, reginoids, zinc salts, and salicylazosulfapyridin (Salazopyrin).

According to the invention, the present compounds are administered to a patient suffering from one of the above mentioned pathological conditions in a daily dose (for adults) from 0.2 mg to 7000 mg, preferably from 1–3500 mg, and in the veterinary practice correspondingly in daily doses from 0.5 to 100 mg/kg bodyweight.

The invention will now be further described in the following non-limiting Examples:

EXAMPLE 1

(2R,3R;2S,3S)-3-[3-(2-Quinolylmethoxy)-anilino]-2-hydroxy-3-phenyl propionic acid, sodium salt To a solution of 3-(2'-quinolylmethoxy)aniline (1.25 g, 5 mmol) in 20.0 ml ethanol is added a solution of (±)trans-3-phenyloxirane carboxylic acid sodium salt (0.95 g, 5 mmol) in water (5.0 ml) and ethanol (15.0 ml). The reaction mixture is refluxed for 24 hours. After cooling to room temperature, the white precipitate is filtered off, washed with ethanol and ether and dried in air. It is obtained as a dihydrate with a melting point of 136°–145° C. The acid was prepared from this sodium salt as yellow crystals with a melting point of 229°–231° C.

EXAMPLE 2

(2R,3R;2S,3S)-3-[4-(2-Quinolylmethyloxy)-anilino]-2-hydroxy-3-phenyl propionic acid, sodium salt By following the procedure of Example 1, but replacing 3-(2'-quinolylmethoxy)aniline with 4-(2'-quinolylmethoxy)aniline the title compound is obtained as a dihydrate with a melting point of 250°–260° C.

EXAMPLE 3

(2R,3R;2S,3S)-3-[2-(2-Quinolylmethyloxy)-anilino]-2-hydroxy-3-phenyl propionic acid, sodium salt By following the procedure of Example 1, but replacing 3-(2'-quinolylmethoxy)aniline with 2-(2'-quinolylmethoxy)aniline, the title compound is obtained as a hydrate with a melting point of 85°–110° C.

EXAMPLE 4

(2R,3R;2S,3S)-3-[3-(2-Quinolylmethyloxy)-anilino]-2-hydroxy-3-phenyl propionic acid ethyl ester A solution of 3-(2-quinolylmethoxy)aniline (2.5 g, 10 mmol) and trans(±)ethyl-3-phenylglycidate (2.5 ml) in ethanol (50 ml) is refluxed for 3 hours. After cooling, the solution is evaporated in vacuo, the residue is triturated with hydrochloride acid, and the title compound is obtained. It is isolated as the dihydrochloride with a melting point of 209°–211° C.

EXAMPLES 5–10

By following the procedure of Example 4 and using the appropriate starting materials, compounds of Table 1 are obtained as racemic mixtures (2R,3R;2S,3S).

TABLE 1

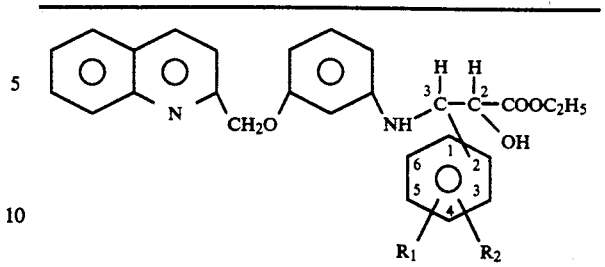

| Ex. No. | R₁ | R₂ | Melting point | Remarks |
|---|---|---|---|---|
| 5 | 2-CH₃ | H | 187–192° C. | Dihydrochloride |
| 6 | 2-CH₃O— | H | 172–178° C. | Dihydrochloride |
| 7 | 2-Cl— | H | 177–183° C. | Hydrochloride, hydrate |
| 8 | 2-F— | H | 194–203° C. | Dihydrochloride |
| 9 | 3-Cl— | H | 206–215° C. | Dihydrochloride |
| 10 | 2-Cl | 4-Cl— | 187–191° C. | Dihydrochloride |

EXAMPLE 11

(2S,3R;2S,3S)-3-[4-(2-Quinolylmethyloxy)-anilino]-2-hydroxy-3-phenyl propionic acid ethyl ester A mixture of 4-(2-quinolylmethyloxy)aniline (0.25 g, 1 mmol) and trans(±)ethyl-3-phenylglycidate (0.25 ml) in ethanol (5 ml) is refluxed for 3 hours. After cooling, the resulting precipitate is collected by filtration, and washed with ethanol. The title compound is obtained with a melting point of 157°–159° C.

EXAMPLE 12

(2R,3R)-3-[3-(2-quinolylmethyloxy)-anilino]-2-hydroxy-3-phenyl propionic acid, sodium salt By following the procedure of Example 1, but replacing (±)trans-3-phenyloxirane carboxylic acid sodium salt with (−)trans-3-phenyloxirane carboxylic acid, sodium salt (Lit. K. Harada, J. Org. Chem. 31 (1966) p. 1407), the title compound is obtained as a trihydrate.
Melting point 120°–126° C.
$[\alpha]_D^{25} = -50.5$ (c=1, 1n HCl),
$[\alpha]_D^{25} = +26.0$ (c=1, MeOH).

EXAMPLE 13

(2S,3S)-3-[3-(2-quinolylmethyloxy)-anilino]-2-hydroxy-3-phenyl propionic acid, sodium salt By following the procedure of Example 1, but replacing (±)trans-3-phenyloxirane carboxylic acid sodium salt with (+)trans-3-phenyloxirane carboxylic acid, sodium salt, the title compound is obtained as a trihydrate.
Melting point 120°–125° C.
$[\alpha]_D^{25} = +50.4$ (c=1, 1n HCl),
$[\alpha]_D^{25} = -25.5$ (c=1, MeOH).

EXAMPLE 14

(2R,3R;2S,3S)-3-[3-(2-Quinolylmethyloxy)-anilino]-2-hydroxy-3-phenyl propionic acid, sodium salt a) 3-(3-Hydroxyanilino)-2-hydroxy-3-phenyl propionic acid sodium salt.

By following the procedure of Example 1, but replacing 3-(2-quinolylmethyloxy)aniline with 3-hydroxyaniline, the title compound is obtained as a hydrate with a melting point of 143°–145° C.

b) A mixture of 3-(3-hydroxyanilino)-2-hydroxy-3-phenyl propionic acid, sodium salt, 2-bromomethylquinoline, sodium carbonate and dimethylformamide is stirred overnight at room temperature. The mixture is filtered, and the resulting solution is partially concentrated. The product is triturated with water, and the title compound is obtained. Melting point 136°–145° C.

EXAMPLE 15

(S,R)-2-[3-(2-Quinolylmethyloxy)-anilino]-2-phenyl acetic acid 3-(2-Quinolylmethyloxy)aniline, 2H$_2$O (8.0 g, 28 mmol), ethyl-α-bromophenylacetate (8.0 ml, 45 mmol) and potassium carbonate (7.0 g, 50 mmol) were stirred overnight in 75 ml of dimethylformamide. Water (300 ml) was added, and the reaction mixture was extracted with diethylether (3×100 ml). the combined diethylether extracts were extracted with water (2×250 ml) and dried with MgSO$_4$ before a charcoal treatment. Diethylether was evaporated in vacuo, and the residual oil (16 g) was dissolved in methanol (50 ml), acetone (50 ml) and methanolic potassium hydroxide solution (50 ml, 6.4N). The mixture was refluxed for 2½ hours, evaporated to dryness and dissolved in water (300 ml), pH was slowly adjusted to 5.5 by adding 4N acetic acid. The precipitated product was filtered off and dried to give the crude title compound (10.3 g). Recrystallisation rom acetone/methanol gave 7.5 g of the title compound.

EXAMPLE 16

(S,R)-2-[4-(2-Quinolylmethyloxy)-anilino]-2-phenyl acetic acid ethyl ester 4-(2-Quinolylmethyloxy)aniline (9.7 g, 30 mmol), ethyl α-bromophenylacetate (10 ml, 56.8 mmol) and potassium carbonate (22 g, 159 mmol) were stirred for 2 days at room temperature in dimethylformamide (100 ml). Water (150 ml) was added slowly precipitating the product. The liquid was decanted, and the rest was dissolved in ethyl acetate (200 ml) at 70° C. The ethyl acetate phase was extracted with water at 70° C. (2×75 ml) and still at 70° C. dried with MgSO$_4$ and filtered. The product was precipitated by addition of heptane during evaporation in vacuo. The title compound was filtered off, washed with hexane and dried to give 7.1 g.

EXAMPLE 17

(S,R)-2-[4-(2-Quinolylmethyloxy)-anilino]-2-phenyl acetic acid

2-[4-(2-Quinolylmethyloxy)-anilino]-2-phenyl acetic acid ethyl ester (6.5 g, 11 mmol) was refluxed for 4 hours in a mixture of acetone (15 ml), methanol (15 ml) and methanolic potassium hydroxide solution (15 ml, 6.0N). The reaction mixture was evaporated to dryness and dissolved in ethyl acetate (100 ml) and water (100 ml). pH was adjusted to 5.5 and ethyl acetate was evaporated in vacuo. The title compound was filtered off, washed with water (50 ml) and dried to give 5.2 g.

EXAMPLES 18–24

By following the procedure of Example 11 and using the appropriate starting materials, compounds of Table 2 are obtained as racemates (2R,3R;2S,3S).

TABLE 2

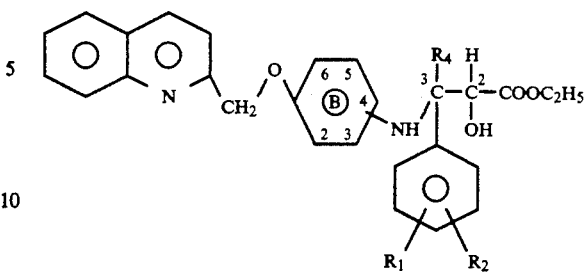

| Ex. No. | Position of bond in ring B | R$_1$ | R$_2$ | R$_4$ | Melting point |
|---|---|---|---|---|---|
| 18 | 3' | 3-F— | H | H | 114–116° C. |
| 19 | 3' | 4-F— | H | H | 122–128° C. |
| 20 | 3' | 4-Cl— | H | H | 133–135° C. |
| 21 | 3' | 4-CH$_3$— | H | H | 122–123° C. |
| 22 | 3' | 4-CH$_3$O— | H | H | 120–122° C. |
| 23 | 3' | 4-NO$_2$— | H | H | 101–106° C. |
| 24 | 4' | H | H | CH$_3$— | 166–168° C. |

EXAMPLES 25–40

By following the procedure of Example 1 and using the appropriate starting materials (Method A) or hydrolysis of the appropriate ethyl esters (Example 17) (Method B), compounds of Table 3 are obtained as racemates (2R,3R;2S,3S).

TABLE 3

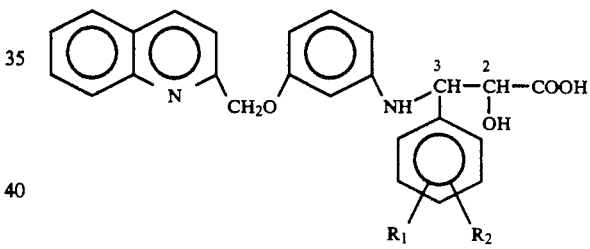

| Ex. No. | R$_1$ | R$_2$ | Melting point | Method of Preparation | Remarks |
|---|---|---|---|---|---|
| 25 | 2-CH$_3$— | H | 89–91° C. | B | Na-salt |
| 26 | 2-F— | H | 121–123° C. | B | Na-salt, trihydrate |
| 27 | 2-Cl— | H | 81–83° C. | B | Na-salt |
| 28 | 2-CH$_3$O— | H | 108–110° C. | B | Na-salt trihydrate |
| 29 | 3-Cl— | H | 87–89° C. | B | Na-salt trihydrate |
| 30 | 3-F— | H | 138–140° C. | A and B | Na-salt, dihydrate |
| 31 | 4-CH$_3$— | H | 234–236° C. | B | |
| 32 | 4-F— | H | 229–230° C. | B | Semihydrate |
| 33 | 4-F— | H | 149–151° C. | B | Na-salt dihydrate |
| 34 | 4-Cl— | H | 115–119° C. | B | Na-salt trihydrate |
| 35 | 4-Cl— | H | >245° C. | B | |
| 36 | 4-CH$_3$O— | H | 191–191° C. | B | |
| 37 | 4-NO$_2$— | H | 140–142° C. | B | Na-salt, trihydrate |
| 38 | 2-F— | 5-F— | 127–129° C. | A | Na-salt trihydrate |
| 39 | 2-F— | 4-F— | 86–98° C. | A | Na-salt trihydrate |
| 40 | 2-Cl— | 4-Cl— | 94–98° C. | B | Na-salt dihydrate |

EXAMPLE 41

(2R,3R;2S,3R)-3-[3-(2-Quinolylmethyloxy)-anilino]-2-hydroxy-3-phenyl propionic acid, sodium salt By following the procedure of Example 1, but replacing (±)trans-3-phenyloxirane carboxylic acid, sodium salt with (±)cis-3-phenyloxirane carboxylic acid, sodium salt (Lit. L. Thijs et al, Tetrahedron Vol. 46 (1990), p 2611), the title compound is obtained as a dihydrate.

Melting point >250° C.

EXAMPLE 42

(2R,3S)-3-[3-(2-Quinolylmethyloxy)-anilino]-2-hydroxy-3-phenyl propionic acid, sodium salt By following the procedure of Example 41, but using (−)-(2R,3R)-cis-3-phenyloxirane carboxylic acid, sodium salt (Lit. L. Thijs et al, Tetrahedron Vol. 46 (1990), p 2611), the (2R,3S)-form of the title compound was obtained.

EXAMPLE 43

(2R,3R)-3-[3-(2-Quinolylmethyloxy)-anilino]-2-hydroxy-3-phenyl propionic acid, sodium salt By following the procedure of Example 41, but using (+)-(2S,3S)-cis-3-phenyloxirane carboxylic acid, sodium salt (Lit. L. Thijs et al, Tetrahedron Vol. 46 (1990), p 2611), the (2S,3R)-form of the title compound was obtained.

EXAMPLE 44

| Aerosol | |
|---|---|
| (2R,3R;2S,3S)-3-[3-(2-Quinolylmethyloxy)-anilino]-2-hydroxy-3-(4-fluorophenyl) propionic acid, semihydrate (the active substance) | 1000 mg |
| Sorbitan trioleate | 700 mg |
| Monofluorotrichloromethane | 595 g |
| Difluorodichloromethane | 798 g |

The active substance is micronized in a jet-mill. The majority of the particles should be less than 5 μm in diameter.

A drug concentrate is prepared by dissolving sorbitan trioleate in a small amount of monofluorotrichlormethane and adding the active substance. The concentrate is homogenized carefully. The concentrate is transferred to a sealed tank provided with a refrigeration system. The remaining propellants are added under stirring and cooling to −50° C.

Suitable aerosol container are filled with the calculated amount of formulation and sealed immediately with metering valves with suitable actuators. Each puff delivers 50 μg of the active substance.

EXAMPLE 45

| Capsule | |
|---|---|
| (2R,3R;2S,3S)-3-[3-(2-Quinolylmethyloxy)-anilino]-2-hydroxy-3-(2-fluorophenyl) propionic acid, sodium salt, trihydrate (active substance) | 100 mg |
| Lactose fine crystalline | 197 mg |
| Magnesium stearate | 3 mg |

The active substance is mixed in a suitable mixer with lactose until a homogeneous state is reached. The magnesium stearate is added, and the blending procedure is continued for a few minutes. By means of a suitable capsule-filling machine hard gelatine capsules size 0 are filled, each with 300 mg of the mixture.

EXAMPLE 46

| Tablet | |
|---|---|
| (2R,3R;2S,3S)-3-[3-(2-Quinolylmethyloxy)-anilino]-2-hydroxy-3-(4-fluorophenyl) propionic acid, sodium salt, dihydrate (active substance) | 100 mg |
| Lactose | 75 mg |
| Starch | 12 mg |
| Methyl cellulose | 2 mg |
| Sodium carboxymethyl cellulose (CMC-Na) | 10 mg |
| Magnesium stearate | 1 mg |

The active substance, lactose and starch are mixed to a homogeneous state in a suitable mixer and moistened with a 5 percent aqueous solution of methylcelluose 15 cps. The mixing is continued until granules are formed. If necessary, the wet granulation is passed through a suitable screen and dried to a water content of less than 1% in a suitable dryer, e.g. fluid bed or drying oven. The dried granulation is passed through a 1 mm screen and mixed to a homogeneous state with CMC-Na. Magnesium stearate is added, and the mixing is continued for a short period of time.

Tablets with a weight of 200 mg are produced from the granulation by means of a suitable tabletting machine.

EXAMPLE 47

| Suppository | |
|---|---|
| (2R,3R;2S,3S)-3-[3-(2-Quinolylmethyloxy)-anilino]-2-hydroxy-3-(2-chlorophenyl) propionic acid, sodium salt (active substance) | 100 mg |
| Cocoa butter | 1900 mg |

Cocoa butter is slowly heated to form a melt not exceeding 40° C. The active substance is incorporated in the melt, and suppositories with a weight of 2 grams are prepared by moulding.

EXAMPLE 48

| Topical formulation | | | |
|---|---|---|---|
| I | (2R,3R;2S,3S)-3-[3-(2-Quinolylmethyloxy)-anilino]-2-hydroxy-3-(3-chlorophenyl) propionic acid, sodium salt, trihydrate (active substance) | | 2% w/w |
| II | Cetostearyl alcohol | | 10% w/w |
|  | Liquid paraffin | | 10% w/w |
|  | White soft paraffin | | 5% w/w |
|  | Polyoxyethylene sorbitane monostearate | | 5% w/w |
| III | Methylparaben | | 0.2% w/w |
|  | Glycerol | | 10% w/w |
|  | Water to make | | 100% w/w |

The ingredients stated under II are melted together and heated to 70° C. in a vessel fitted with stirrer and homogenizer. In another vessel, the water phase (III) is prepared by heating to 70° C. The water phase is slowly added to the oil phase with continuous stirring and homogenization.

The active substance is added, and the temperature is kept for 15 minutes at 70° C. The vessel is cooled to 40° C. under continuous stirring and homogenization. The cooling is continued to a temperature below 25° C. under slow stirring.

EXAMPLE 49

| Formulation for injection | |
|---|---|
| (2R,3R)-3-[3-(2-Quinolylmethyloxy)-anilino]-2-hydroxy-3-phenyl propionic acid, sodium salt (active substance) | 1% |
| Sodium chloride | q.s. |
| Water for injection to make | 100% |

The active substance is dissolved in water for injection. The solution is made isotonic with sodium chloride. The solution is filled into ampoules and sterilized.

EXAMPLE 50

| Ophthalmic solution | |
|---|---|
| (2R,3R;2S,3S)-3-[3-(2-Quinolylmethyloxy)-anilino]-2-hydroxy-3-(2-fluorophenyl)propionic acid, sodium salt, trihydrate (active substance) | 0.2% |
| Mannitol | 5% |
| Hydroxyethylcellulose | 0.5% |
| Phenyl ethyl alcohol | 0.5% |
| Water for injection to make | 100% |

A 2 percent concentrate of hydroxyethylcellulose in water for injection including phenyl ethyl alcohol is prepared by slowly spreading the cellulose on the water surface. The concentrate is allowed to stand for complete swelling of the cellulose.

The active substance and mannitol are dissolved in the remaining amount of water for injection.

The solutions are carefully mixed together and sterilized. Under aseptic conditions the solution is filled into suitable sterile containers.

What we claim is:

1. A compound of the formula I

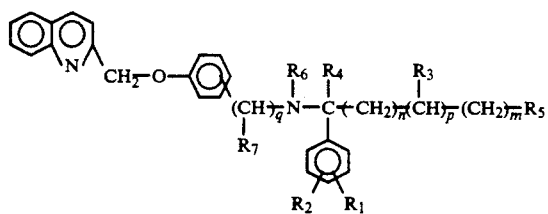

in which m and n stands for an integer from 0–5, p stands for 0 or 1, and q stands for an integer from 0–4, $R_1$ and $R_2$ are the same or different and stand for hydrogen, halogen, nitro, amino, alkyl or alkoxy; $R_3$ is hydroxy, hydrogen, straight or branched, saturated or unsaturated $C_{1-6}$ alkyl; $R_5$ stands for carboxy, 1H-tetrazolyl, a sulphonic acid group, a sulfamyl group, a sulphinic acid group, or a hydroxamic acid group; $R_4$ and $R_6$ are the same or different and stand for hydrogen, straight or branched, saturated or unsaturated $C_{1-6}$ alkyl groups or aralkyl groups; $R_7$ has the same meaning as $R_5$ or represents a hydrogen, straight or branched, saturated or unsaturated $C_{1-6}$-alkyl group; and pharmaceutically acceptable, non-toxic salts and in-vivo hydrolyzable alkyl, acyloxyalkyl, alkoxycarbonyloxyalkyl or aminoacyloxyalkyl esters thereof.

2. A salt according to claim 1, in which the salt is selected from the group consisting of salts formed with hydrochloric, hydrobromic and hydroiodic acid, phosphoric acid, sulphuric acid, nitric acid, p-toluenesulphonic acid, methanesulphonic acid, formic acid, acetic acid, propionic acid, citric acid, tartaric acid, and maleic acid, alkali metal salts and alkaline earth metal salts, as well as salts with ammonia and non-toxic amines.

3. A compound of claim 1 which is selected from the group consisting of the following acids or esters, their salts and pure enantiomeric forms:

(2R,3R;2S,3S)-3-[3-(2-quinolylmethyloxy)-anilino]-2-hydroxy-3-phenyl propionic acid;
(2R,3R;2S,3S)-3-[4-(2-quinolylmethyloxy)-anilino]-2-hydroxy-3-phenyl propionic acid;
(2R,3R;2S,3S)-3-[2-(2-quinolylmethyloxy)-anilino]-2-hydroxy-3-phenyl propionic acid;
(2R,3R)-3-[3-(2-quinolylmethyloxy)-anilino]-2-hydroxy-3-phenyl propionic acid;
(2S,3S)-3-[3-(2-quinolylmethyloxy)-anilino]-2-hydroxy-3-phenyl propionic acid;
(2R,3R;2S,3S)-3-[3-(2-quinolylmethyloxy)-anilino]-2-hydroxy-3-phenyl propionic acid;
(S,R)-2-[3-(2-quinolylmethyloxy)-anilino]-2-phenyl acetic acid;
(S,R)-2-[4-(2-quinolylmethyloxy)-anilino]-2-phenyl acetic acid;
(2R,3R;2S,3S)-3-[3-(2-quinolylmethyloxy)-anilino]-2-hydroxy-3-phenyl propionic acid;
(2R,3R;2S,3S)-3-[3-(2-quinolylmethyloxy)-anilino]-2-hydroxy-3-(2-fluorophenyl)propionic acid;
(2R,3R;2S,3S)-3-[3-(2-quinolylmethyloxy)-anilino]-2-hydroxy-3-(2-chlorophenyl)propionic acid;
(2R,3R;2S,3S)-3-[3-(2-quinolylmethyloxy)-anilino]-2-hydroxy-3-(2-methoxyphenyl)propionic acid;
(2R,3R;2S,3S)-3-[3-(2-quinolylmethyloxy)-anilino]-2-hydroxy-3-(3-chlorophenyl)propionic acid;
(2R,3R;2S,3S)-3-[3-(2-quinolylmethyloxy)-anilino]-2-hydroxy-3-fluorophenyl)propionic acid;
(2R,3R;2S,3S)-3-[3-(2-quinolylmethyloxy)-anilino]-2-hydroxy-3-(4-methylphenyl)propionic acid;
(2R,3R;2S,3S)-3-[3-(2-quinolylmethyloxy)-anilino]-2-hydroxy-3-(4-fluorophenyl)propionic acid;
(2R,3R;2S,3S)-3-[3-(2-quinolylmethyloxy)-anilino]-2-hydroxy-3-(4-chlorophenyl)propionic acid;
(2R,3R;2S,3S)-3-[3-(2-quinolylmethyloxy)-anilino]-2-hydroxy-3-(4-methoxyphenyl)propionic acid;
(2R,3R;2S,3S)-3-[3-(2-quinolylmethyloxy)-anilino]-2-hydroxy-3-(4-nitrophenyl)propionic acid;
(2R,3R;2S,3S)-3-[3-(2-quinolylmethyloxy)-anilino]-2-hydroxy-3-(2,5-difluorophenyl)propionic acid;
(2R,3R;2S,3S)-3-[3-(2-quinolylmethyloxy)-anilino]-2-hydroxy-3-(2,4-difluorophenyl)propionic acid;
(2R,3R;2S,3S)-3-[3-(2-quinolylmethyloxy)-anilino]-2-hydroxy-3-(2,4-dichlorophenyl)propionic acid;
(2R,3R;2S,3S)-3-[3-(2-quinolylmethyloxy)-anilino]-2-hydroxy-3-phenyl propionic acid ethyl ester;
(2R,3R;2S,3S)-3-[3-(2-quinolylmethyloxy)-anilino]-2-hydroxy-3-(4-methoxyphenyl)propionic acid ethyl ester.

4. A pharmaceutical composition comprising a compound according to claim 1 and a pharmaceutically acceptable carrier therefor.

5. A method of inhibiting 5-lipoxygenase and thereby the production and effects of leukotrienes in a host in need of such inhibition, said method comprising administering to said host an effective amount of a compound according to claim 1.

* * * * *